United States Patent
Braun et al.

(10) Patent No.: US 6,511,497 B1
(45) Date of Patent: Jan. 28, 2003

(54) VASCULAR FILTER SYSTEM

(75) Inventors: Michael Braun, Backnang (DE); John S. Geis, Grünwald (DE)

(73) Assignee: Cormedics GmbH, Deisenhofen (DE)

( * ) Notice: Subject to any disclaimer, the term of this patent is extended or adjusted under 35 U.S.C. 154(b) by 300 days.

(21) Appl. No.: 09/661,461

(22) Filed: Sep. 13, 2000

(30) Foreign Application Priority Data

Sep. 14, 1999 (DE) .................................. 299 16 162 U

(51) Int. Cl.$^7$ ............................................... A61M 29/00
(52) U.S. Cl. ........................................................ 606/200
(58) Field of Search ................................. 606/159, 200, 606/194, 191, 192, 195, 198, 108, 127, 112, 114; 604/104, 93.01, 96.01, 99.01

(56) References Cited

U.S. PATENT DOCUMENTS

| 4,425,908 | A |   | 1/1984  | Simon |   |
|---|---|---|---|---|---|
| 4,688,553 | A |   | 8/1987  | Metals |   |
| 4,832,055 | A | * | 5/1989  | Palestrant | 128/899 |
| 5,324,304 | A | * | 6/1994  | Rasmussen | 606/200 |
| 5,709,704 | A | * | 1/1998  | Nott et al. | 606/200 |
| 5,893,869 | A | * | 4/1999  | Barnhart et al. | 606/200 |
| 5,928,261 | A |   | 7/1999  | Ruiz |   |
| 5,941,896 | A | * | 8/1999  | Kerr | 606/192 |
| 6,007,558 | A | * | 12/1999 | Ravenscroft et al. | 606/194 |
| 6,053,932 | A | * | 4/2000  | Daniel et al. | 606/200 |
| 6,277,139 | B1 | * | 8/2001  | Levinson et al. | 606/200 |
| 6,336,934 | B1 | * | 1/2002  | Gilson et al. | 606/159 |
| 6,342,063 | B1 | * | 1/2002  | DeVries et al. | 606/200 |
| 6,361,546 | B1 | * | 3/2002  | Khosravi | 606/200 |
| 6,391,044 | B1 | * | 5/2002  | Yadav et al. | 606/200 |
| 6,425,909 | B1 | * | 7/2002  | Dieck et al. | 606/200 |

FOREIGN PATENT DOCUMENTS

| DE | 3417738  | 11/1985 |
| DE | 4030998  | 4/1991  |
| DE | 68902516 | 2/1993  |
| FR | 2768326  | 3/1999  |
| WO | 98/33443 | 8/1998  |
| WO | 98/49952 | 11/1998 |
| WO | 99/16382 | 4/1999  |
| WO | 99/44510 | 9/1999  |

* cited by examiner

*Primary Examiner*—A. Vanatta
(74) *Attorney, Agent, or Firm*—Dickstein Shapiro Morin & Oshinsky LLP

(57) ABSTRACT

The present invention comprises a vascular filter system for non-permanent application which is provided with a guide wire, a filter membrane having an inner area provided in the area of the proximal end of the guide wire and a free outer area, and an umbrella structure provided at least on the outer area of the filter membrane, made of a flexible material and permitting opening and closing of the umbrella formed by the umbrella structure and filter membrane, characterized in that the system has contactless structure for closing the umbrella. The structure can be of a magnetic nature or involve mechanisms based on temperature changes.

8 Claims, 4 Drawing Sheets

VASCULAR FILTER SYSTEM

BACKGROUND OF THE INVENTION

This invention relates to a vascular filter system, in particular a vascular filter system having a guide wire, a filter membrane and an umbrella structure, the filter membrane having an inner area provided in the area of the proximal end of the guide wire and a free outer area, and the umbrella structure being made of a flexible material and permitting opening and closing of the umbrella formed by the umbrella structure and filter membrane.

A great number of, for example angioplastic, surgical and non-surgical methods have been developed for removing deposits in blood vessels. These methods, along with the implantation of bypasses at sites affected by stenoses, involve the danger of parts of the plaque or thrombi coming loose and ending in an embolism. In order to prevent such a danger, vascular filters have been developed which are intended to block micro- and macroparticles.

Such a vascular filter is described for example in WO 98/33443. This conventional vascular filter is formed by an opening mechanism. In its open position the filter is substantially perpendicular to the axis of the guide wire via which it can be introduced into the blood vessel. For removal from the blood vessel, conventional vascular filters provide recuperating threads. These can be fastened to the outer circumference of the filter and are operated via a wire which can be guided in the guide wire for example. Recuperation of the filter, e.g. at the end of surgery, requires the application of a sufficient force via the wire connected with the recuperating threads. Since in most methods the site where the filter is introduced into the vessel is far away from the site where the filter is used, the length of the guide wire and recuperating wire is considerable. In surgery on the carotid for example one usually introduces the filter via the artery in the groin. The guide wire and thus also the recuperating wire can thereby have lengths of more than one meter. In order to permit application of the forces necessary for recuperating the filter at a distance of this size, the forces exerted on the recuperating wire must be great.

Due to these great forces and considerable length, as well as the fact that the guide wire must follow the course of the blood vessel and can therefore not be guided through the body straight, the guide wire as well as the recuperating wire and recuperating threads can get caught in conventional vascular filter systems. This can considerably impede and prolong the process of recuperating or folding up and removing the filter. This lengthens the time of the total surgery, which can be serious for the patient, in particular due to the required narcotics. In addition, jammed wires can cause injuries to the blood vessel.

SUMMARY OF THE INVENTION

The invention is therefore based on the problem of providing a vascular filter system that does not have the disadvantages of the prior art, is in particular easy and reliable to handle, and reduces the danger of injury to the patient and the strain of longer operating times.

The invention is based on the finding that this problem can be solved by a vascular filter system requiring either no, or a very low, expenditure of force for closing the filter over the length between the site of entry into the body and the site of the filter.

The problem is solved according to the invention by a vascular filter system having contactless means for closing the umbrella.

The inventive vascular filter system is preferably used for non-permanent application.

The inventive system has the advantage that the structure of the umbrella can be simple. No mechanical connections are required between the filter membrane or umbrella structure, on the one hand, and an element extending from the position of the filter to the site where the filter system enters the body, on the other hand. Also, this simple structure prevents a mechanical connection from getting caught, jamming or tearing. This further reduces the risk for the patient. Finally, contactless means can be activated from outside without requiring a great expenditure of force over the length between the position of the filter and the site where the filter system enters the body. This can also prevent injuries or the guide wire and recuperating element getting caught.

In the inventive vascular filter system the umbrella structure is made is a flexible material allowing opening and closing of the umbrella structure. Preferably, the umbrella structure therefore involves a spring which in the released state supports the open umbrella. The spring can consist of a flexible, wire-shaped material bent in a zigzag shape for example, a coil spring or also a flexible wire-shaped material coated with a coil spring. Activation of the umbrella structure material causes the structure to contract, thereby compressing the spring. The spring force of the umbrella structure is preferably selected such that, firstly, sufficient pressure is produced against the wall of the blood vessel in the open state and, secondly, the force for folding up or closing the umbrella is so low that it can be provided by contactless means.

According to an embodiment of the invention, the closing means are given by the umbrella structure material. The umbrella structure is provided at least on the outer area of the filter membrane. If the material of said structure is selected so as to contract under certain circumstances, this causes closing of the umbrella. In this embodiment one can for example use materials which contract through chemical or physical activation, thereby causing closing of the umbrella. Since activation takes place in the blood vessel, i.e. in the body, one must select materials whose activation is safe. One can activate by introducing media into the blood in the area of the filter. Further, one can use materials which contract through the action of radiation.

According to a further embodiment, closing means are additionally provided on the guide wire. These means can cooperate with the means given by the umbrella structure material. The activation of the umbrella structure material necessary for contracting the umbrella structure can in this case be produced by the means provided on the guide wire. The means can either be fastened directly to the guide wire or disposed displaceably thereon.

In the former case, the means are preferably disposed in the area of the guide wire against which the umbrella structure lies after folding up. In the latter case, the means can be fastened for example to a catheter pushed over the guide wire, i.e. carried thereby. In this embodiment it is only necessary to bring the means from a position at a certain distance from the umbrella into the position where it can cooperate with the umbrella structure and closing of the umbrella is effected. The path over which the catheter must be pushed is therefore very small and in particular smaller than the path over which a recuperating wire must be pushed according to the embodiments of the prior art. In addition, for pushing the catheter used according to the invention one need only apply the force for moving the catheter as such.

This force is much lower than that necessary for mechanically folding up the umbrella via recuperating wire and recuperating threads against the bloodstream.

According to a preferred embodiment, the means provided on the guide wire are a magnetic catheter. In this embodiment, the magnetic catheter can be threaded onto the guide wire. The magnet is provided on the end of the catheter facing the proximal end of the guide wire. It may be a permanent magnet or else a temporarily activable one, e.g. an electromagnet. In this embodiment the magnetic catheter serves as a displacing element for the magnet as such, thus allowing exact positioning of the magnet with respect to the position of the filter.

According to a further preferred embodiment, the umbrella structure material is activable by temperature changes, i.e. contracts upon a temperature change, thereby causing closing of the umbrella. In this embodiment the umbrella structure is preferably formed from a nitinol spring. This material, which is a Ti—Ni alloy, has the advantage of firstly contracting when cold and secondly having a shape memory, i.e. showing a so-called memory effect. The shape in which the umbrella optimally covers the cross section of the blood vessel to be treated can therefore be specified for the umbrella structure, and a contraction of the umbrella structure toward this shape memory obtained by briefly introducing a cold medium, for example ice water.

According to a further embodiment, the umbrella structure material is magnetizable. This quality of the umbrella structure material permits activation of the material by magnetism by means provided on the guide wire. Further, it is possible to form the umbrella structure such that bars of magnetizable material extend radially from the inner area of the filter membrane fastened to the guide wire to the outer area of the filter membrane. For opening the umbrella the bars can be homopolar so that they repel each other, and for closing they can be polarized alternately so that they attract each other.

In a preferred embodiment, the filter system has a guide sheath for receiving the guide wire and umbrella. Said guide sheath can serve firstly to permit the umbrella to be introduced into the blood vessel without injuring the blood vessel, and secondly as a holding device for the closed umbrella upon removal of the filter. The umbrella is preferably withdrawn into the sheath via the guide wire after the closing process and cannot expand again, or only slightly, if the guide sheath diameter is suitably selected. This permits the umbrella to be held in the folded up position without requiring further apparatuses after the closing means are deactivated, e.g. the magnet switched off or the addition of ice water stopped.

The guide sheath can serve in addition as a conduit for media to be brought into the area of the umbrella for effecting activation of the umbrella structure material, i.e. its contraction, e.g. as a conduit for ice water.

The invention will be described further in the following with reference to the enclosed drawing showing possible embodiments of the invention but not restricting the scope of protection.

DETAILED DESCRIPTION OF THE PREFERRED EMBODIMENTS

Corresponding parts are designated with the same reference numbers in the individual figures.

Figure 1:
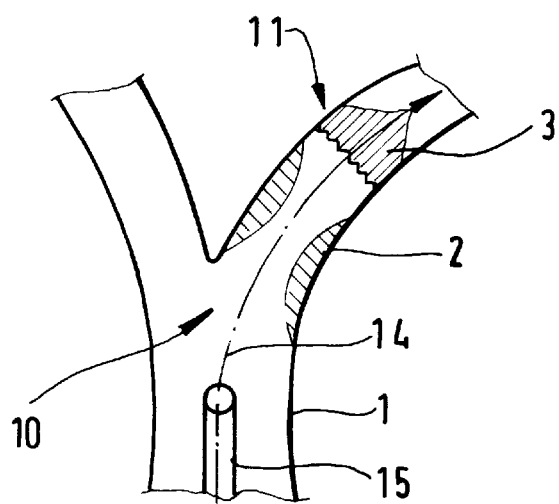
FIG. 1 shows an embodiment of the inventive vascular filter system in its application.

FIG. 1 shows vascular filter system 10 introduced into blood vessel 1. Umbrella 11 is open in blood vessel 1 so as to cover its cross section and lie against the wall of blood vessel 1 over a certain area. Below umbrella 11 stenoses 2 are indicated. Said stenoses leading to constriction of the blood vessel are to be removed by the methods using inventive vascular filter system 10. When said stenoses are removed, particles (thrombi) 3 are detached, being caught and entrained by the bloodstream. FIG. 1 shows that said thrombi are caught in the umbrella. The umbrella is fastened to guide wire 14. Said guide wire extends in the position shown in FIG. 1 beyond the end of guide sheath 15 and is guided therein.

Figure 2:
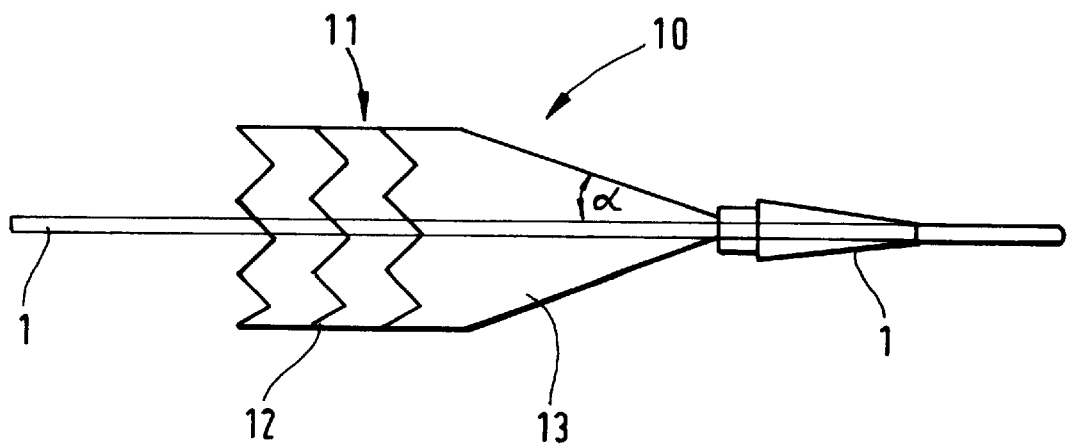
FIG. 2 shows a schematic representation of an embodiment.

FIG. 2 schematically shows the structure of inventive vascular filter system 10. Guide wire 14 has a proximal end provided with tip 141. Tip 141 facilitates introduction of vascular filter system 10 and prevents injuries to the blood vessel upon introduction. Adjacent to tip 141 the inside part of filter membrane 13 is fastened to guide wire 14. The filter membrane extends in the shown embodiment at an angle of less than 90° from guide wire 14 in the radial direction. The outer area of filter membrane 13, however, is aligned approximately parallel to the axis of guide wire 14. In the outer area umbrella structure 12 is further provided. In the shown embodiment, umbrella structure 12 is provided in a zigzag along the outer circumference of filter membrane 13 and parallel thereto in the outer area of filter membrane 13. The position in FIG. 2 shows umbrella 11 in its open form.

Figure 3A:
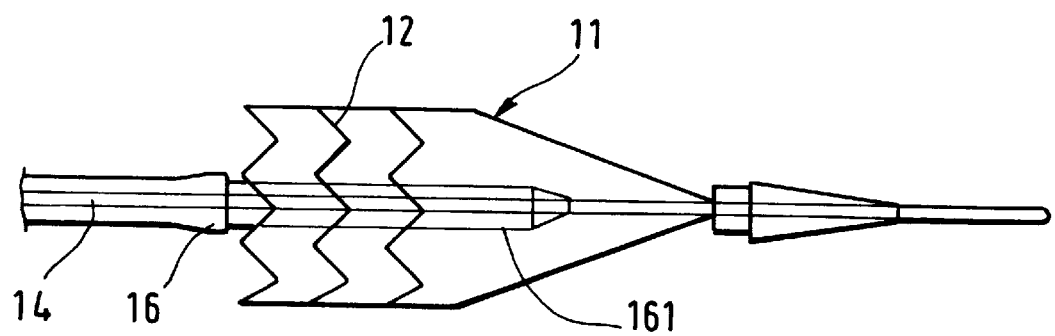
FIG. 3a shows a schematic representation of an embodiment of the invention with a magnetic catheter with the umbrella open.
Figure 3B:
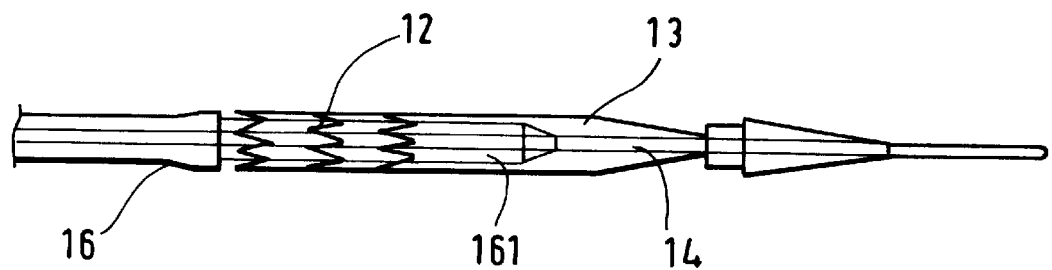
FIG. 3b shows a schematic representation of an embodiment of the invention with a magnetic catheter with the umbrella closed.

FIG. 3a schematically shows an embodiment of the invention with magnetic catheter 16 with umbrella 11 open. Magnetic catheter 16 is threaded onto guide wire 14. The catheter has magnet 161 at its end facing umbrella 11. In this embodiment, umbrella structure 12 is made of a magnetizable material. When magnetic catheter 16 is pushed into umbrella 11 far enough for the material of umbrella structure 12 to interact with magnet 161, umbrella structure 12 is magnetized and umbrella 11 closed by the magnetic effect. Thus, both magnetic catheter 16 guided on guide wire 14 and the material of umbrella structure 12 form the means for closing umbrella 11 here. The closed position of umbrella 11 is shown in FIG. 3b.

In this position, umbrella 11 together with magnet 161 can be withdrawn into a guide sheath (not shown). Guide sheath and umbrella can thus be safely removed from the blood vessel.

Figure 4A:
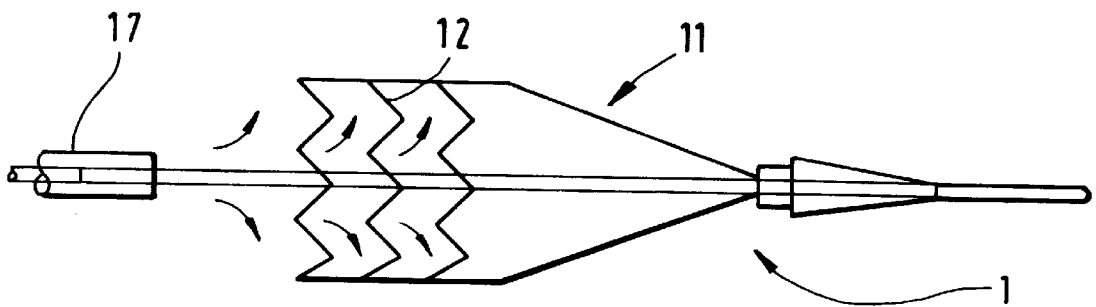
FIG. 4a shows a schematic representation of a further embodiment of the invention with the umbrella open.
Figure 4B:
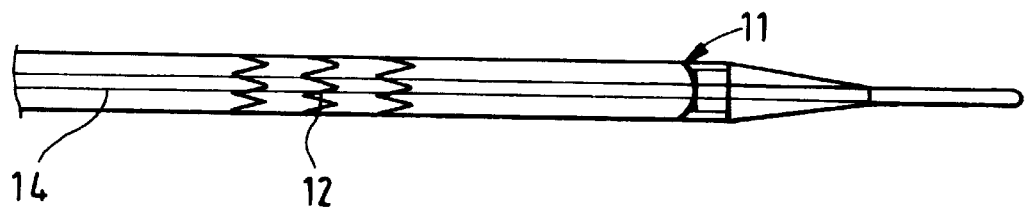
FIG. 4b shows a schematic representation of a further embodiment of the invention with the umbrella closed.

FIG. 4a shows a further embodiment of inventive vascular filter system 10. In this embodiment, umbrella structure 12 is formed by temperature-sensitive material. Said material contracts when temperature decreases. When a cold medium, e.g. ice water, is brought into the area of umbrella structure 12 via catheter 17 as indicated by the arrows in FIG. 4a, the umbrella structure contracts, causing closing of umbrella 11. The supply of cold medium is continued until umbrella 11 has assumed the position shown in FIG. 4b. In this position umbrella 11 can be drawn into a guide sheath (not shown) and removed therewith from the blood vessel.

Figure 5A:
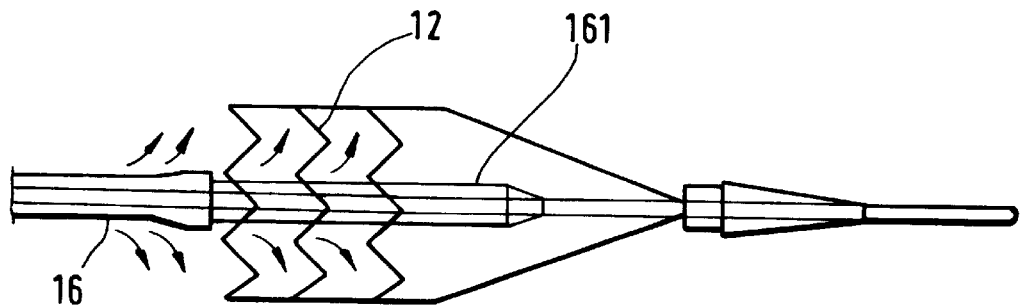
FIG. 5a shows a schematic representation of a further embodiment of the invention with a magnetic catheter with the umbrella open.
Figure 5B:
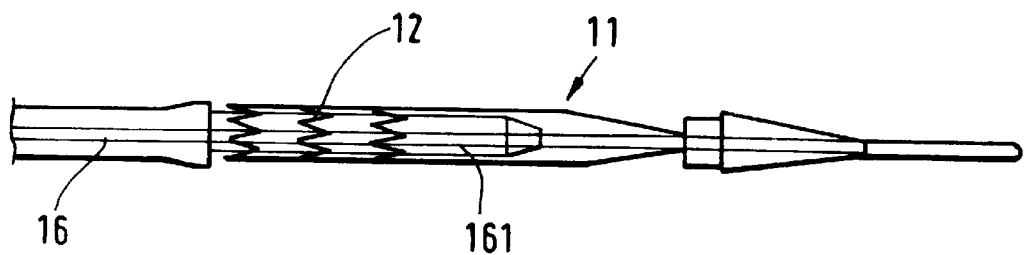
FIG. 5b shows a schematic representation of a further embodiment of the invention with a magnetic catheter with the umbrella closed.

FIG. 5a shows an embodiment in which both magnetic catheter 16 and supply via further catheter 17 (not shown here) can be used. In this embodiment, umbrella structure 12 is formed by material which is firstly temperature-sensitive and secondly magnetizable. It is also possible, however, to make umbrella structure 12 out of two materials which are either processed together or exist in separate threads or springs, each of the materials having one of the stated properties. This embodiment utilizes both the effect of the means constituted by the temperature-sensitive material and the effect of the cooperation of magnet 161 and at least part of umbrella structure 12. FIG. 5b shows this embodiment in the closed state of umbrella 11.

Figure 6A:
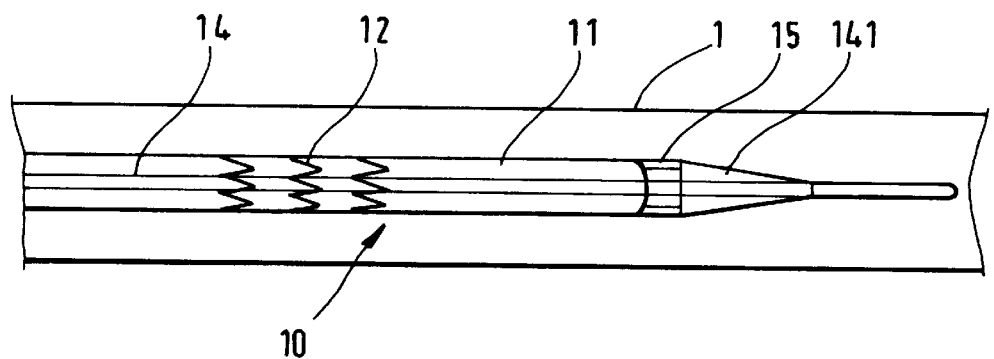
FIG. 6a shows a schematic representation of a further embodiment of the invention with a guide sheath in the closed state.

FIG. 6a shows the state in which vascular filter system 10 without a magnetic catheter is introduced into blood vessel 1 and removed again.

Guide sheath 15 encloses umbrella 11 and extends up to tip 141 of guide wire 14. When guide sheath 15 is withdrawn over umbrella 11, the latter can open. In accordance with the material of umbrella structure 12, umbrella 11 opens due to the shape memory of the material or due to spring force. A combination of these two causes is also conceivable.

Figure 6B:
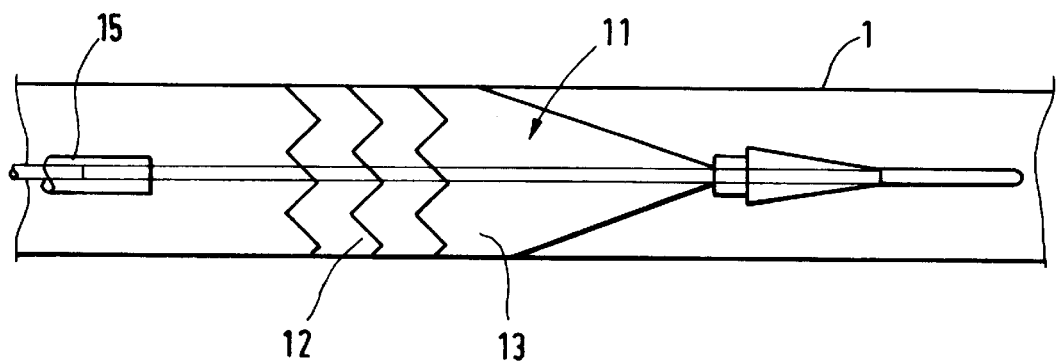
FIG. 6b shows a schematic representation of a further embodiment of the invention with a guide sheath in the open state.

After the opening of umbrella 11 the state shown in FIG. 6b is given. Guide sheath 15 is located behind umbrella 11, viewed from the tip of guide wire 14. The umbrella lies against the wall of blood vessel 1, thereby preventing thrombi from passing beside the filter.

After the end of treatment, medium can be brought into the area of the umbrella through guide sheath 15, or the material of umbrella structure 12 activated otherwise, e.g. by radiation. This causes contraction of umbrella 11. In the embodiment of the filter shown in the figures, the outer area of filter membrane 13 will contract. This prevents thrombi caught in umbrella 11 from being squeezed out.

Umbrella 11 can also have besides umbrella structure 12 in the outer area further umbrella structure 12 extending in the form of struts from guide wire 14 to the outer area of filter membrane 13. Said struts ensure that umbrella 11 has a certain stability and lies close against guide wire 14 or optionally magnetic catheter 16 after contraction, thus being drawn into guide sheath 17 without obstacles.

After withdrawal, vascular filter system 10 again has the form shown in FIG. 6a and can be easily removed from blood vessel 1.

The filter material is called "filter membrane" according to this invention. Possible filter membranes are meshes or braids, as well as other porous materials having sufficient flexibility to allow opening and closing of the umbrella without damaging the material. The material can be of a textile nature. It is also within the scope of the invention to make the filter membrane out of a magnetizable material. This supports the process of closing the umbrella. One can use for example meshes or braids of metal.

The form of the umbrella preferably extends in the open state substantially in the direction parallel to the axis of the guide wire, i.e. in the longitudinal direction. One can in particular use stocking-like umbrellas capable of receiving particles in the inner area of the filter membrane. This reduces the danger of particles being squeezed out during closing.

For the umbrella structure one can use magnetizable or temperature-sensitive materials depending on the embodiment. It is in particular preferable to use self-expanding springs made of this material. One can in particular use materials with shape memory.

The form of the umbrella structure can have different designs. One can use wires, preferably with a spring effect, but also bands of the material. Besides the form provided in the figures, the umbrella structure can also be constituted by bars extending over the surface of the filter membrane from the guide wire to the outer circumference. Spiral-shaped arrangements of the umbrella structure can also be realized within the scope of the invention. It is essential to the invention that the umbrella structure is present at least in the outer area of the filter membrane. By providing the umbrella structure in this area one can cause reliable closing of the umbrella and prevent particles from escaping from the filter membrane.

As a guide wire one can use all wires known for such purposes in the field of medicine.

The dimensions of the vascular filter system depend on the intended use, e.g. the diameter of the blood vessel to be treated. The guide wire can have for example a diameter of 0.014 to 0.035 inches. The guide sheath can have a diameter of for example 1.67 to 3.33 mm (5 to 10 Fr). The diameter of the open umbrella can be for example 3 to 10 mm, and the umbrella in the closed state can have a length of for example 10 to 50 mm. The optionally provided area of the umbrella with which it lies against the blood vessel wall can be e.g. 5 to 20 mm long.

What is claimed is:

1. A vascular filter system for non-permanent application comprising:

a guide wire, a filter membrane having an inner area provided in the area of the proximal end of the guide wire and a free outer area, and an umbrella structure provided at least on the outer area of the filter membrane, made of a flexible material and permitting opening and closing of the umbrella formed by the umbrella structure and filter membrane, characterized in that the system has contactless means for closing the umbrella.

2. A vascular filter system according to claim 1, characterized in that the means for closing the umbrella are given by the material of the umbrella structure.

3. A vascular filter system according to claims 1 or 2, characterized in that means for closing the umbrella are additionally provided on the guide wire.

4. A vascular filter system according to claim 3, characterized in that the means provided on the guide wire constitute a magnetic catheter.

5. A vascular filter system according to claims 1 or 2, characterized in that the material of the umbrella structure is activable by temperature change.

6. A vascular filter system according to claims 1 or 2, characterized in that the umbrella structure is formed from a nitinol spring.

7. A vascular filter system according to claims 1 or 2, characterized in that the material of the umbrella structure is magnetizable.

8. A vascular filter system according to claims 1 or 2, characterized in that the filter system has a guide sheath for receiving the guide wire and umbrella.

* * * * *